United States Patent
Kitazumi et al.

(10) Patent No.: US 9,630,889 B2
(45) Date of Patent: Apr. 25, 2017

(54) SYSTEM FOR PRODUCING ORGANIC FERTILIZER AND A FEED FROM EXCRETA OF DOMESTIC ANIMAL

(71) Applicant: E's Inc., Minato-ku, Tokyo (JP)

(72) Inventors: Kazushige Kitazumi, Minato-ku (JP); Mikio Matsushima, Minato-ku (JP); Yasuharu Nakano, Minato-ku (JP); Yaroslava Polutova, Minato-ku (JP); Koji Nagae, Minato-ku (JP); Ryoichi Sekiya, Minato-ku (JP); Hisaki Yamawaki, Minato-ku (JP)

(73) Assignee: E's Inc., Toyko (JP)

( * ) Notice: Subject to any disclaimer, the term of this patent is extended or adjusted under 35 U.S.C. 154(b) by 0 days.

(21) Appl. No.: 14/427,497

(22) PCT Filed: Oct. 15, 2013

(86) PCT No.: PCT/JP2013/077892
§ 371 (c)(1),
(2) Date: Mar. 11, 2015

(87) PCT Pub. No.: WO2014/065148
PCT Pub. Date: May 1, 2014

(65) Prior Publication Data
US 2015/0223496 A1     Aug. 13, 2015

(30) Foreign Application Priority Data
Oct. 26, 2012 (JP) .................................. 2012-236439

(51) Int. Cl.
*C05F 3/06* (2006.01)
*A01K 67/033* (2006.01)
(Continued)

(52) U.S. Cl.
CPC .............. *C05F 3/06* (2013.01); *A01K 67/033* (2013.01); *A23K 10/20* (2016.05); *A23K 10/26* (2016.05);
(Continued)

(58) Field of Classification Search
CPC .... A23K 1/1873; A23K 1/106; A23K 1/1826; A23K 1/188; A23K 1/10; C05F 3/06;
(Continued)

(56) References Cited

U.S. PATENT DOCUMENTS 7,998,728 B2 *   8/2011   Rhoads ............... C05F 17/0009
                                                  119/6.7
2012/0131970 A1 *   5/2012   Chang ....................... C05F 3/00
                                                   71/12
(Continued)

FOREIGN PATENT DOCUMENTS

JP     10-245289 A    9/1998
JP     2002-11440 A    1/2002
(Continued)

OTHER PUBLICATIONS

International Search Report of PCT/JP2013/077892, dated Jan. 14, 2014. [PCT/ISA/210].
(Continued)

Primary Examiner — Korie H Chan
(74) Attorney, Agent, or Firm — Sughrue Mion, PLLC

(57) ABSTRACT

This invention provides a system for producing organic fertilizer from excreta of domestic animal obtained by digesting of larvae belonging to Diptera such as *Musca domestica* (housefly), *Boettcherisca peregrine* and *Tabanus*, and for producing grown larvae which can be used as a feed for cultured fish and chicken raising. In an embodiment, the system for producing organic fertilizer from excreta of domestic animal and for producing grown larvae which can (Continued)

be used as a feed for cultured fish and chicken raising is characterized by arranging a plurality of nurturing-processing storage units for nurturing larvae hatched from eggs, and a means for dislodging only larvae forcibly from a former nurturing-processing storage unit to a later nurturing-processing storage unit successively with the progress of growth of larvae, wherein larvae leave said former nurturing-processing storage unit autonomously.

18 Claims, 5 Drawing Sheets

(51) Int. Cl.
| | | |
|---|---|---|
| B09B 3/00 | (2006.01) | |
| C05F 3/00 | (2006.01) | |
| C02F 3/32 | (2006.01) | |
| B09B 5/00 | (2006.01) | |
| C05F 17/00 | (2006.01) | |
| A23K 10/20 | (2016.01) | |
| A23K 10/26 | (2016.01) | |
| A23K 50/75 | (2016.01) | |
| A23K 50/90 | (2016.01) | |
| A23K 50/80 | (2016.01) | |

(52) U.S. Cl.
CPC .............. *A23K 50/75* (2016.05); *A23K 50/80* (2016.05); *A23K 50/90* (2016.05); *B09B 3/00* (2013.01); *B09B 5/00* (2013.01); *C02F 3/32* (2013.01); *C05F 3/00* (2013.01); *C05F 17/0009* (2013.01); *B09B 2220/04* (2013.01); *Y02P 20/145* (2015.11); *Y02W 30/43* (2015.05)

(58) Field of Classification Search
CPC .......... C05F 17/0009; C05F 3/00; B09B 5/00; B09B 3/00; B09B 2220/04; C02F 3/32; A01K 67/033; Y02P 20/145; Y02W 30/43
USPC ......................................................... 119/6.5
See application file for complete search history.

(56) References Cited

U.S. PATENT DOCUMENTS

2012/0135120 A1* 5/2012 Chang .................... A23K 50/90
426/465
2014/0123902 A1* 5/2014 Kitazumi ............. A01K 67/033
119/6.5

FOREIGN PATENT DOCUMENTS

| JP | 2005132683 A | * | 5/2005 |
| JP | 2012-116665 A | | 6/2012 |
| RU | 2050138 C1 | | 12/1995 |

OTHER PUBLICATIONS

Communication dated Jun. 16, 2016 from the Patent Office of the Russian Federation issued in corresponding Application No. 2015115476.

* cited by examiner

SYSTEM FOR PRODUCING ORGANIC FERTILIZER AND A FEED FROM EXCRETA OF DOMESTIC ANIMAL

CROSS REFERENCE TO RELATED APPLICATIONS

This application is a National Stage of International Application No. PCT/JP2013/077892 filed Oct. 15, 2013, claiming priority based on Japanese Patent Application No. 2012-236439, filed Oct. 26, 2012, the contents of all of which are incorporated herein by reference in their entirety.

TECHNICAL FIELD

This invention relates to a system for producing organic fertilizer and feed by using enzymatic decomposition of excreta of domestic animal which is effected in a body of an insect belonging to Diptera such as *Musca domestica* (housefly), *Boettcherisca peregrine* and *Tabanus*.

STATE OF THE ART

In livestock facilities such as pig firming and diary firming, excreta are discharged every day and an amount of excreta is generally proportional to a breeding number of animals. Usually, the excreta are composted by means of microorganisms. Disposal of excreta by microorganisms, however, consume too long time and in some areas, the livestock excreta generated in large quantities are left on ground without treatment, resulting in contamination of ground water, which has become a cause of social problems. Therefore, how to dispose of excreta is a problem to be solved today. In particular, it is not allowed any more to damp unsanitary excreta which give off a bad smell due to the recent severe regulation for environmental protection.

An amount of excreta of livestock is increasing along with expansion of the livestock scale but it is not easy to dispose of excreta generated daily in a large quantity efficiently in a short period of time. Therefore, disposal of livestock excreta is a heavy burden for livestock farmers. Under such situation, it was proposed to use an insect bio-processing system for processing animal excreta so as to reduce the above burden (see Patent Document 1 of JP-A1-2002-11440).

The insects bio-processing system disclosed in Patent Document 1 comprises a means for conveying sequentially processing-containers on which animal excreta are placed, a means for feeding animal excreta onto an empty processing-container conveyed successively, a means to depositing eggs or larvae of housefly into unfermented excreta in the processing containers, a means for maturing excreta for a require duration in the processing containers stacked in multiple stages, a means to collect larvae or pupa metamorphosed from the larvae of housefly crawling out of the processing-containers, and a means for recovering finished or matured excreta from the processing-container which is advanced successively.

In this insect bio-processing system, reduction of harm or detoxification of excreta can be realized by feeding or feeding animal excreta to housefly.

Patent Document 2 of JA-A1-2011-100358 which is another invention of this applicant proposes an organic fertilizer producing system for producing organic fertilizer and feed, from excreta of livestock or domestic animal by using larvae of *Musca domestica* (housefly), comprising a first nurturing-processing storage unit for nurturing or growing larvae hatched from eggs, a plurality of second nurturing-processing storage units arranged below the first nurturing-processing storage unit, grown larvae dropping onto the second nurturing-processing storage units by utilizing such a behavior of larvae that they crawl out of the first nurturing-processing storage unit, the above processing being reaped for required several times, wherein the excreta of livestock are decomposed with enzyme within larvae bodies during larvae are nurtured in each nurturing-processing storage unit, while the larvae excrete or produce an organic fertilizer base material, a collecting section for collecting the organic fertilizer base material produced, and a larvae collecting section for collecting grown larvae crawling out of the final nurturing-processing storage unit.

PRIOR ARTS

Patent Document

[Patent Document 1] JP-A1-2002-11440
[Patent Document 2] JA-A1-2011-100358

DISCLOSURE OF THE INVENTION

Problems to be Solved by the Present Invention

However, in the insect bio-processing system disclosed in Patent Document 1, reduction of harm or detoxification of excreta is done by feeding animal excreta to an insect belonging to Diptera such as *Musca domestica* (housefly), *Boettcherisca peregrine* and *Tabanus*, all treatment and handling for producing organic fertilizer from housefly larvae must be carried out in a processing chamber whose temperature and humidity are adjustable. Still more, all of deposition of eggs of an insect belonging to Diptera such as *Musca domestica* (housefly), *Boettcherisca peregrine* and *Tabanus* onto excreta placed in a container, of hatching of eggs, of growing of larvae, and loading and unloading of the containers must be done manually. Moreover, larvae crawling out of the containers must be handled manually, since this method utilizes such a habit of an insect belonging to Diptera such as *Musca domestica* (housefly), *Boettcherisca peregrine* and *Tabanus* those larvae come out a medium to become pupae after larvae grow in certain level. However, working environment in the processing chamber to carry out the above works is extremely poor and is not amenable to manual labor, because the work environment is filled with odor of excreta and grown larvae (maggots) are crawling all around.

Still moreover, there is another problem. An amount of food or feed processed by the larvae of houseflies increases explosively in a week when there is enough breeding volume and food. On the contrary, if such enough breeding volume and food are not available, an amount of organic fertilizer base material which is produced within the bodies of larvae by enzymatic decomposition and excreted out of larvae decrease and the growth of larvae become also slow.

In the system for producing organic fertilizer and feed disclosed in Patent Document 2, there are such problems that a plurality of nurturing-processing storage units must be stacked in multi-levels, supply of the food to larvae is apt to be short, advance of larvae take a longer time, and advancing movement of larvae is not sure, because this system utilize such a habit of insects that they fall by themselves naturally.

The present invention was done in view of the above problems of prior arts and provides a method for producing organic fertilizer by utilizing a capacity of housefly for possessing excreta of domestic animal.

In the present invention, a sufficient nurturing area is assured for larvae and a sufficient amount of food can be supplied to larvae to accelerate their growth, so that an amount of excrete produced within the body of larva by enzymatic decomposition of livestock excreta can be increased. And, larvae are forcibly displaced from a nurturing-processing storage unit at a predetermined time, so that separation between larvae and the resulting organic fertilizer can be performed at a desired time schedule. Still more, manual handling operation can be reduced or eliminated. Thus, the present invention provides a system which can produce organic fertilizer from animal excreta efficiently with less labor and which can produce grown larvae as a feed for cultured fish and chicken raising.

SUMMARY OF THE INVENTION

In order to solve the above problems, an invention defined in claim 1 is a system for producing organic fertilizer from excreta of domestic animal by using insect larvae belonging to Diptera such as *Musca domestica* (housefly), *Boettcherisca peregrine* and *Tabanus*, and for producing grown larvae which can be used as a feed for cultured fish and chicken raising, characterized by a plurality of nurturing-processing storage units for nurturing larvae or larvae hatched from eggs, and a means for dislodging only larvae forcibly from a former nurturing-processing storage unit to a later nurturing-processing storage unit successively with the progress of growth of larvae, wherein larvae leave the former nurturing-processing storage unit autonomously.

An invention defined in claim 2 is a system for producing organic fertilizer from excreta of domestic animal as a food by using insect larvae belonging to Diptera such as *Musca domestica* (housefly), *Boettcherisca peregrine* and *Tabanus*, and for producing grown larvae which can be used as a feed for cultured fish and chicken raising, characterized by a first nurturing-processing storage unit for raising larvae hatched from eggs, the first nurturing-processing storage unit being supplied at a predetermined time interval with a predetermined quantity of the food and a predetermined number of eggs, a second nurturing-processing storage unit having a larger volume than the first nurturing-processing storage unit, larvae hatched from the eggs as well as the food being displaced from the first nurturing-processing storage unit to the second nurturing-processing storage unit, at a time when the larvae hatched from the eggs reach predetermined weights, wherein the second nurturing-processing storage unit is supplied with a fresh food to fatten up the larvae, a third nurturing-processing storage unit into which only larvae are forcibly dislodged from the second nurturing-processing storage unit at a time when the food is consumed, wherein the third nurturing-processing storage unit is supplied with a fresh food to fatten further up the larvae, wherein a digested residue of the food in the second nurturing-processing storage unit is recovered as a fertilizer, and the larvae are forcibly displaced from the third nurturing-processing storage unit to a recovery section at a time when the food is consumed, a digested residue of the food in the third nurturing-processing storage unit is recovered as a fertilizer, and the larvae in the recovery section are collected as a feed for other animal.

An invention defined in claim 3 is a system for producing organic fertilizer from excreta of domestic animal as a food by using insect larvae belonging to Diptera such as *Musca domestica* (housefly), *Boettcherisca peregrine* and *Tabanus*, and for producing grown larvae which can be used as a feed for cultured fish and chicken raising, characterized by a first nurturing-processing storage unit for raising larvae hatched from eggs, the first nurturing-processing storage unit being supplied at a predetermined time interval with a predetermined quantity of the food and a predetermined number of eggs, a second nurturing-processing storage unit having a larger volume than the first nurturing-processing storage unit and is supplied with a fresh food to fatten up the larvae, wherein only larvae hatched from the eggs are displaced from the first nurturing-processing storage unit to the second nurturing-processing storage unit at a time when the larvae hatched from the eggs reach predetermined weights, and a digested residue of the food in the second nurturing-processing storage unit is recovered as a fertilizer, a third nurturing-processing storage unit into which only larvae are forcibly dislodged from the second nurturing-processing storage unit at a time when the food is consumed, wherein the third nurturing-processing storage unit is supplied with a fresh food to fatten further up the larvae, a digested residue of the food in the third nurturing-processing storage unit being recovered as a fertilizer, the above processing being repeated in further nurturing-processing storage unit having a larger volume than former nurturing-processing storage unit until the final nurturing-processing storage unit which is supplied with a largest amount of a fresh food to fatten up the larvae, wherein only larvae are forcibly dislodged from the final nurturing-processing storage unit to a recovery section at a time when the food is consumed, a digested residue of the food in the final nurturing-processing storage unit being recovered as a fertilizer, while the larvae in the recovery section are collected as a feed for other animal.

An invention defined in claim 4 is a system for producing organic fertilizer and feed according to claim 3, in which a nurturing-processing storage unit into which larvae are forcibly dislodged is positioned at an opposite location, and, after a transfer of larvae completed, a next nurturing-processing storage unit is positioned at an opposite location.

The invention defined in claim 5 is a system for producing organic fertilizer and feed according to any one of claims 1 to 4, characterized in that a transfer means for forcibly dislodging only larvae is selected from means to irradiate light, means to reduce the oxygen concentration, means to increase the concentration of ammonia, means to heat or cool, means to dry and means to decrease the quantity of food, these means being applied to the nurturing-processing storage unit into which forcibly larvae are forcibly dislodged.

The invention defined in claim 6 is a system for producing organic fertilizer and feed according to claim 5, wherein the means to irradiate light is chosen from natural light, blue light, ultraviolet ray and other light of limited wavelength.

The invention defined in claim 7 is a system for producing organic fertilizer and feed according to claim 5, wherein the means to heat or cool is chosen from heater, irradiation, heated stone, ice, cooled water, radiation air conditioning.

The invention defined in claim 8 is a system for producing organic fertilizer and feed according to claim 5, wherein the means to dry is to blowing of dry air.

The invention defined in claim 9 is a The system for producing organic fertilizer and feed according to any one of claims 1 to 8, characterized in that the food is chosen from organic wastes such as animal excreta, viscera of domestic animal, offal of fish, food residue, organic wastes such as sewage treatment residue.

In the organic fertilizer and feed production system according to the present invention, a base material of organic fertilizer is produced inside the bodies of larvae of housefly by enzymatic decomposition when larvae eat excreta of livestock and is excreted out of the larval. Therefore, there is no consumption of fuel which is necessary in case of incineration and an impact on the environment can be reduced, because there is no emotion of carbon dioxide. Still more, unlike the conventional bacterial detoxification, emission of long-lasting bad smell can be reduced or eliminated and there is no propagation or breeding of pathogens. In the system according to the present invention, excreta are disposed and handled safely by utilizing a preying habit of larvae of *Musca domestica* (housefly), *Boettcherisca peregrine* and *Tabanus*.

Still more, in the system according to the present invention, larvae of houseflies are nourished and nurtured in an enough breeding area and volume with sufficient food. Therefore, the preying habit of larvae of houseflies can be improved and a large amount of excreta of livestock such as swine dung can be changed to organic fertilizer efficiently in a shorter period of time. In particular, in the system according to the present invention, the nurturing-processing storage unit is divided or increased gradually with the progress of growth of larvae, so that prey can be distributed uniformly or evenly.

Furthermore, the organic fertilizer base material produced by the system according to the present invention contains abundant chitosan. Such organic fertilizer produced by the system according to the present invention can be used in preparation of organic fertilizer which can improve soil and the antibacterial activity, promote growth of plant, prevent disease of plant, and improve the quality of fruits.

In the system according to the present invention, larvae are forcibly displaced from a nurturing-processing storage unit at a predetermined time, so that separation between larvae and the resulting organic fertilizer can be performed at a desired time schedule, and hence manual handling operation can be reduced or eliminated. Thus, the present invention provides a system which can produce organic fertilizer from animal excreta efficiently with less labor In the system according to the present invention, grown larvae are recovered collectively from the nurturing-processing storage unit and are utilized as an excellent feed.

DETAILED DESCRIPTION OF THE INVENTION

Example 1

Figure 1:
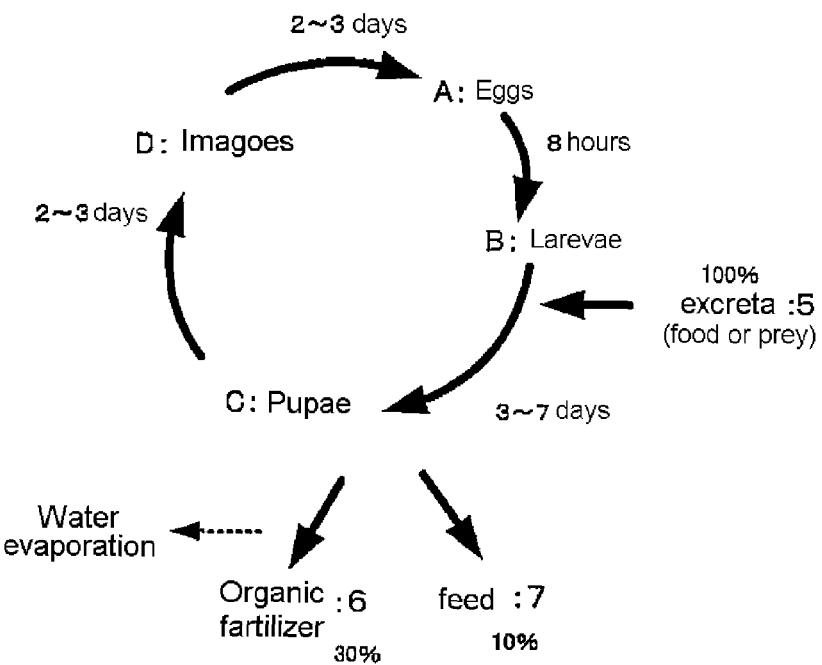
FIG. 1 is a general schematic view of a system for producing organic fertilizer and feed according to the present invention.

To begin with, we will describe a general concept of a system for producing organic fertilizer and feed according to the present invention with reference to Example 1 illustrated in FIG. 1.

In Example 1, housefly eggs or their hatched larvae are utilized as an insect belonging to Diptera such as *Musca domestica* (housefly), *Boettcherisca peregrine* and *Tabanus*. The system of Example 1 is for producing organic fertilizer from the excretory substance of domestic animal as a food and for producing a feed or grown larva as cultured fish and chicken raising.

Figure 2:
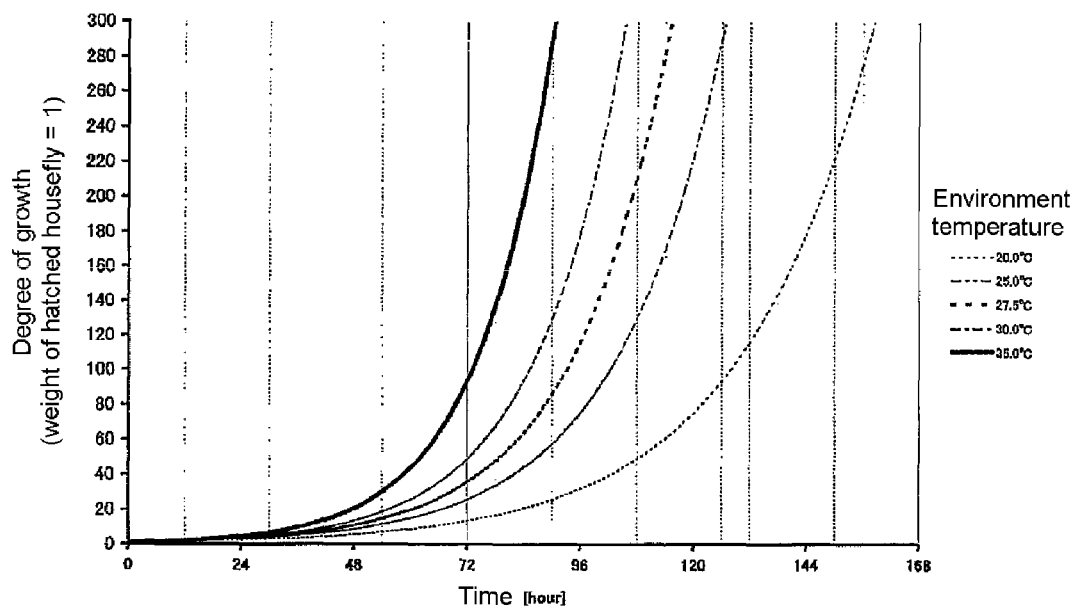
FIG. 2 is a graph showing a change of intake or eating of larvae of houseflies with the progress of their growth.

In the organic fertilizer/feed production system of FIG. 1, imagoes (D) of houseflies lay eggs (A) two to five days after eclosion. A predetermined amount of the eggs (A) of houseflies is supplied into a nurturing-processing storage unit (2) (FIG. 3) on which the food is spread uniformly. The food may be organic wastes such as animal excreta (5), viscera of domestic animal, offal of fish, food residue, and organic wastes such as sewage treatment residue. In Example 1, the food is excreta (5) of pig to fatten the larvae (B). The growth rate of larvae of *Musca domestica* (housefly) is surprising as is revealed in FIG. 2. Their weight change from 0.0001 g just after the eclosion to 0.03 g of after 3 to 7 days or increase 300 times depending to environmental temperature. Similar growth is observed in other Diptera such as *Boettcherisca peregrine* and *Tabanus*

The volume of the nurturing-processing storage unit (2) and the excreta (5) are changed for several times with the growth of larvae (B). The larvae (B) continue eating of excreta (5) for 24 hours and decomposed them with digestive enzyme to change the excreta (5) to organic fertilizer (6). After the larva (B) grow sufficiently, only larvae (B) are forcibly dislodged from the nurturing-processing storage unit, so that the larvae (B) themselves leaves the nurturing-processing storage unit and are collected. Digested residue of the excreta (5) is recovered as organic fertilizer (6).

Majority of larvae collected is sacrificed by boiling and heat-dried to produce a feed (7) for cultured fish and food for livestock. A part of larvae is collected and fed to an egg-making unit (11) (FIG. 3) in which adult houseflies or imagoes (D) are produced from pupae (C) after 2 to 3 days. The resulting imagoes (D) lay eggs in the egg-making unit (11). Thus, a cycle shown in FIG. 1 completes.

The feed (7) contain high percentage of proteins and is suitable as a feed for cultured fish and for livestock. The fertilizer from excreta (5) has an antibacterial activity because they are decomposed with digestive enzyme.

Now, Example 1 according to the present invention is explained with reference of FIG. 3, which show a case in which larvae (B) grows at 300 times from eggs (A) of housefly after 4 days.

Figure 3:
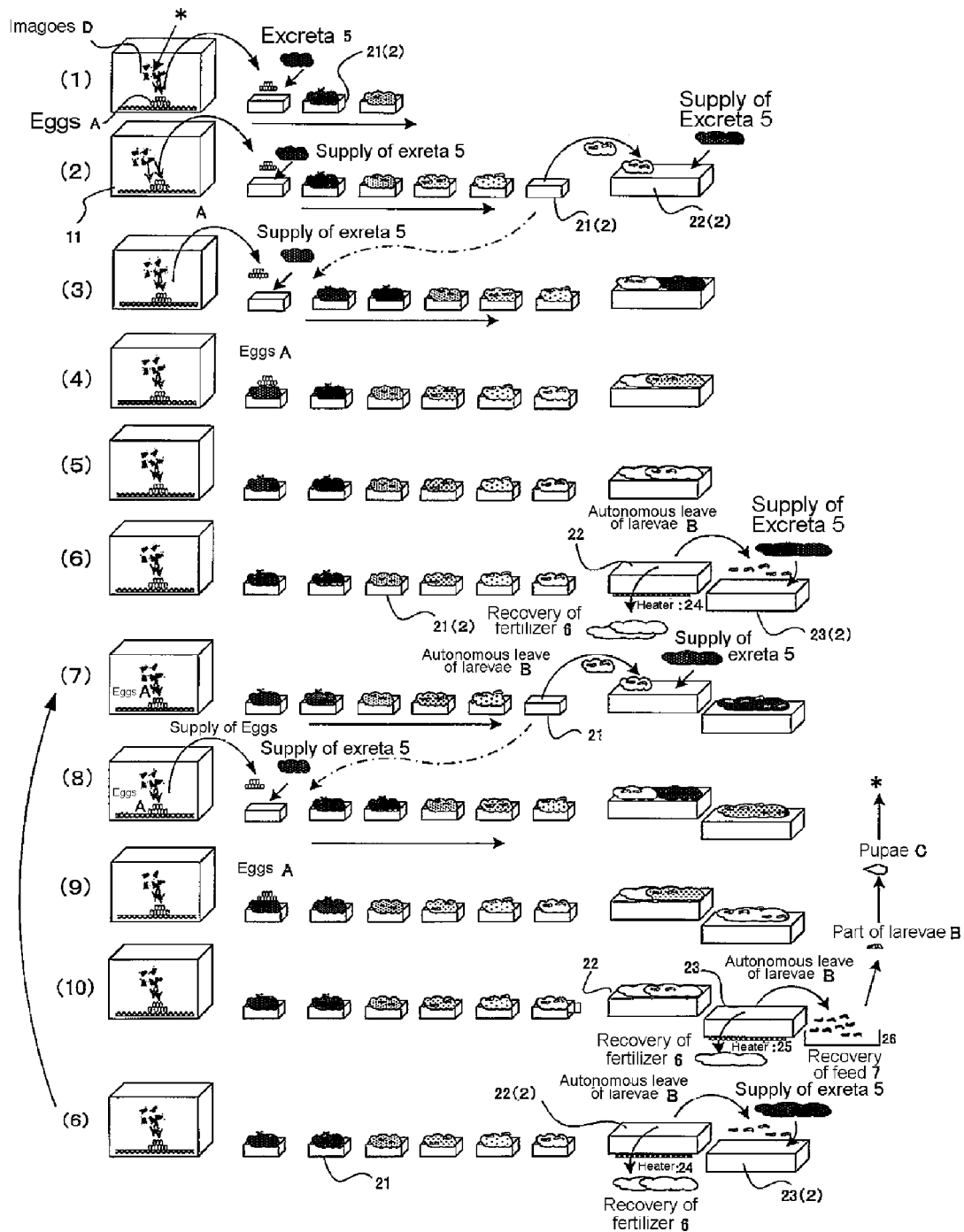
FIG. 3 is an overall illustrative view of a system for producing organic fertilizer and feed of Example 1 according to the present invention.

In a step (1) of FIG. 3, housefly imagoes (D) lay eggs (A) in the egg-making unit (11). A predetermined amount of eggs (A) and a predetermined amount of excreta (5) are supplied to a first nurturing-processing storage unit (21) or tray (1).

In a step (2) of FIG. 3, at intervals of 12 hours, another first nurturing-processing storage unit or tray (21) is provided and fresh eggs (A) and excreta (5) are supplied to the another first nurturing-processing storage unit (21). This operation is repeated for three days. Therefore, there are totally six first nurturing-processing storage units (21) are shown in FIG. 3. In each of the first nurturing-processing storage unit (21), excreta (5) are consumed or ate by larvae (B) (in FIG. 3, the color of excreta (5) turns gradually white). Three days later, almost all excreta (5) are consumed or ate by larvae (B), so that excreta (5) are changed to organic fertilizer (6). The contents (larvae (B) and excreta (5)) in the first nurturing-processing storage units (21) positioned at the right end (in which almost all excreta (5) have been changed to organic fertilizer (6)) are transferred to second nurturing-processing storage unit (22) or tray (2) having a larger volume than the first nurturing-processing storage unit (21). Fresh excreta (5) are supplied to the second nurturing-processing storage unit (22) and nurturing of larvae (B) is continued further.

In a step (3) of FIG. 3, the first nurturing-processing storage unit (21) emptied in the step (2) is recycled (the left end in FIG. 3) and fresh eggs (A) and excreta (5) are supplied to the first nurturing-processing storage unit (21).

In steps (4) and (5), larvae (B) are further nurtured in the first nurturing-processing storage unit (21) and in the second nurturing-processing storage unit (22). In the step (5), excreta (5) have been changed to organic fertilizer (6) in the first nurturing-processing storage unit (21) positioned at the right end and in the second nurturing-processing storage unit or tray (22).

In a step (6), the second nurturing-processing storage unit (22) is heated by a heater (24) to force larvae (B) to leave the second nurturing-processing storage unit (22) and to enter a third nurturing-processing storage unit (23), while the resulting organic fertilizer (6) is obtained from the second nurturing-processing storage unit (22). The third nurturing-processing storage units (23) into which larvae (B) have been transferred is supplied with fresh excreta (5) to continue nurturing of larvae (B).

In a step (7), in each of the first nurturing-processing storage unit (21), excreta (5) are consumed or ate by larvae (B) (in FIG. 3, the color of excreta (5) turns gradually white). The contents (larvae (B) and excreta (5)) in the first nurturing-processing storage units (21) positioned at the right end (in which almost all excreta (5) have been changed to organic fertilizer (6)) are transferred to second nurturing-processing storage unit (22) or tray (2) having a larger volume than the first nurturing-processing storage unit (21). Fresh excreta (5) are supplied to the second nurturing-processing storage unit (22) in which nurturing of larvae (B) is continued further. In the third nurturing-processing storage unit (23) also, nurturing of larvae (B) is continued further.

In a step (8), the first nurturing-processing storage unit (21) emptied in the step (7) is recycled (the left end in FIG. 3) and fresh eggs (A) and excreta (5) are supplied to the first nurturing-processing storage unit (21) or tray (1).

In a step (9), larvae (B) are further nurtured in the first nurturing-processing storage unit (21), in the second nurturing-processing storage unit (22) and in the third nurturing-processing storage unit (23)

In a step (10), the third nurturing-processing storage unit (23) is heated by a heater (25) to force larvae (B) to leave the third nurturing-processing storage unit (23) and to enter a recovery container (26). Majority of larva (B) collected is used as feed (7) for culturing fish and a part of larva (B) is fed to the egg-making unit (11) in which adult houseflies or imagoes (D) are produced from pupae (C). Organic fertilizer (6) is recovered from the emptied third nurturing-processing storage unit (23).

The step (6) restarts after the step (10) and successive steps of from (6) to (10) are repeated cyclically thereafter. Thus, in Example 1, the feed (7) and the organic fertilizer (6) can be recovered at every 12 hours from the third nurturing-processing storage unit (23) in the step (10), and the organic fertilizer (6) can be recovered also from the second nurturing-processing storage unit (22) at every 12 hours. The cycle time can be changed, of course, depending to environmental conditions of growth of larva (B) of Example 1 such as environmental temperature (see FIG. 2).

In Example 1, a heater is used as means for dislodging larvae forcibly from the nurturing-processing storage unit since the control is easy to be done. However, other means such as irradiation and heated stone may be used. Drying can be used as other compulsory dislodging means.

Figure 4:
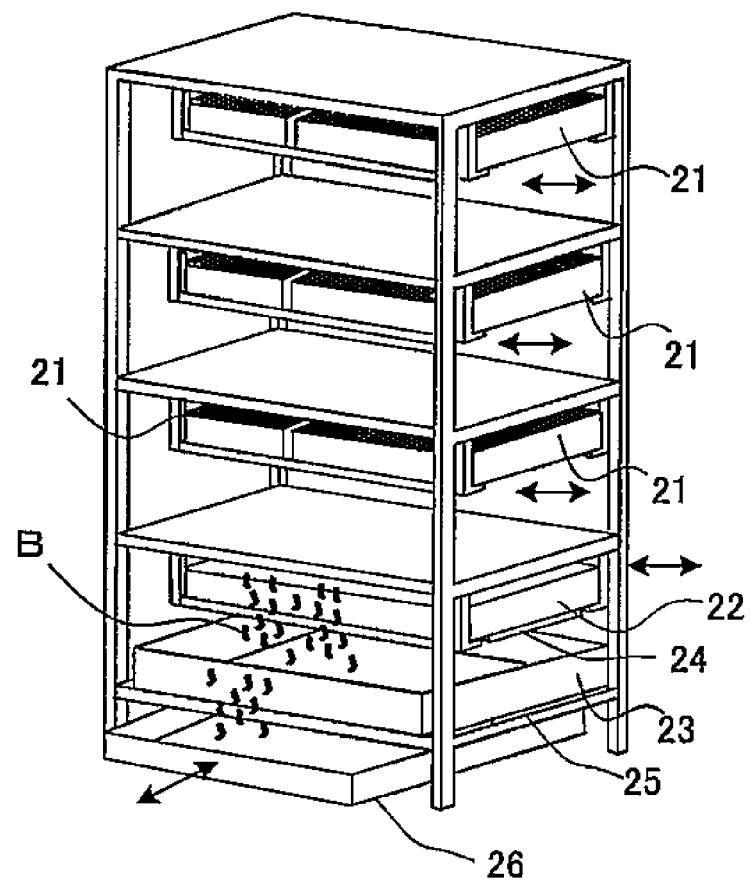
FIG. 4 is a perspective view of nurturing-processing storage units in Example 1.

FIG. 4 shows an embodiment of the nurturing-processing storage units used in Example 1.

Trays in the nurturing-processing storage units (2) shown in FIG. 4 are moved mainly in manual. Upper three shelves are used to store the first nurturing-processing storage units (21) exchangeably. Lower two shelves are used to store the second nurturing-processing storage units (22) (upper) and the third nurturing-processing storage units (23) (bottom) exchangeably respectively.

Into the upper three shelves, the first nurturing-processing storage units (21) are inserted successively so that excreta (5) are changed or consumed into organic fertilizers (6) during every 12 hours. As are shown in the steps (2) and (7), growing larva (B) together with digested organic fertilizers (6) is transferred to the second nurturing-processing storage unit (22). In this case, the second nurturing-processing storage unit (22) has been supplied beforehand with excreta (5), or fresh excreta (5) can be supplied after the transfer.

After larvae (B) grow and produce organic fertilizer (6), a heater (24) is energized, so that larva (B) start an action to leave or craw out of the second nurturing-processing storage unit (22), climb over an edge of thereof and fall onto the third nurturing-processing storage unit (23). Thus, larvae (B) are removed from the second nurturing-processing storage unit (22) autonomously. Organic fertilizer (6) remained in the second nurturing-processing storage unit (22) is recovered.

The transfer means for forcibly dislodging larvae can be other means than the heater, such as irradiation, heated stone, ice, cooled water and radiation air conditioning. The transfer means for forcibly dislodging larvae may be irradiate light, means to reduce the oxygen concentration, means to increase the concentration of ammonia, means to dry and means to decrease the quantity of food. The means to irradiate light may be natural light, blue light, ultraviolet ray and other light of limited wavelength. The means to heat or cool may be blowing of dry air as is used in Example 2.

The third nurturing-processing storage unit (23) has been supplied beforehand with excreta (5), or fresh excreta (5) can be supplied after the transfer, so that larva (B) displaced into the third nurturing-processing storage unit (23) are further fattened just before it metamorphoses in pupae (C).

After larvae (B) grow further and produce much organic fertilizer (6), a heater (25) is energized, so that larva (B) start an action to leave or craw out of the third nurturing-processing storage unit (23), climb over an edge of thereof and fall onto the recovering unit (26). Thus, only larvae (B) are removed from the third nurturing-processing storage unit (23) autonomously. Organic fertilizer (6) remained in the third nurturing-processing storage unit (23) is recovered, while only larva (B) is collected in the recovering unit (26) . . . .

In the system for producing organic fertilizer and a feed according to Example 1 of the present invention, a base material of organic fertilizer is produced inside the bodies of larvae of housefly by enzymatic decomposition when larvae eat excreta of livestock and is excreted out of the larval. Therefore, there is no consumption of fuel which is necessary in case of incineration and an impact on the environment can be reduced, because there is no emission of carbon dioxide. Still more, unlike the conventional bacterial detoxification, emission of long-lasting bad smell can be reduced or eliminated and there is no propagation or breeding of pathogens. In the system according to the present invention, excreta are disposed and handled safely by utilizing a preying habit of larvae of *Musca domestica* (housefly), *Boettcherisca peregrine* and *Tabanus*.

Still more, larvae of houseflies are nourished and nurtured in an enough breeding area and volume with sufficient food. Therefore, the preying habit of larvae of houseflies can be improved and a large amount of excreta of livestock such as swine dung can be changed to organic fertilizer efficiently in a shorter period of time. In particular, the nurturing-processing storage unit is divided or increased gradually with the progress of growth of larvae, so that prey can be distributed uniformly or evenly.

Furthermore, the organic fertilizer base material produced by the system according to the present invention contains abundant chitosan. Such organic fertilizer produced by the system according to the present invention can be used in preparation of organic fertilizer which can improve soil and the antibacterial activity, promote growth of plant, prevent disease of plant, and improve the quality of fruits.

Still more, larvae are forcibly displaced from the second nurturing-processing storage unit (22) and the third nurturing-processing storage unit (23) at a predetermined time, so that separation between larvae and the resulting organic fertilizer can be performed at a desired time schedule, and hence manual handling operation can be reduced or eliminated. Thus, the present invention provides a system which can produce organic fertilizer from animal excreta efficiently with less labor Since a part of larva is collected, and pupae are changed to imagoes which lay eggs, a regenerative recycling system of housefly is realized in the system so that there is no need to supply additional eggs from outside.

The grown larvae are recovered collectively from the third nurturing-processing storage unit (23) and are utilized as an excellent feed.

Example 2

Figure 5A:
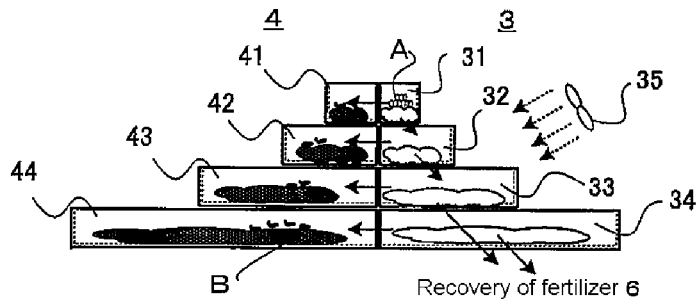
FIGS. 5A-5E are overall illustrative views of a system for producing organic fertilizer and feed of Example 2 according to the present invention.
Figure 5B:
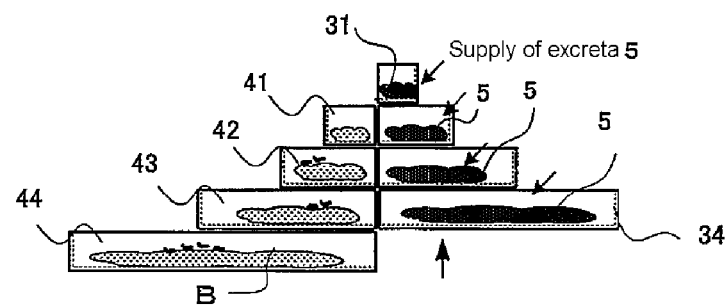
Figure 5C:
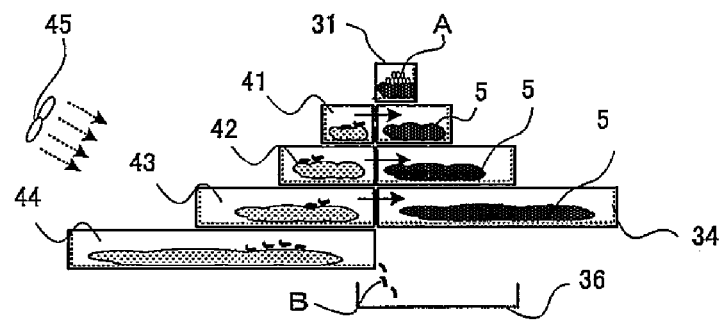

FIGS. 5 (*a*) to (*e*) are side-views of Example 2 illustrating an outline of operations of another system for producing organic fertilizer and a feed according to the present invention. FIG. 6 is a plane view thereof.

The principle of the system for producing organic fertilizer and a feed from excreta of domestic animal by using larvae of housefly according to the present invention is same as Example 1 but Example 2 has a different structure from Example 1 in following point. Namely, a pair of a right side group (3) of nurturing-processing storage units and a left side group (3) of nurturing-processing storage units are arranged or positioned at opposite positions. In each group, a plurality nurturing-processing storage unit is stacked vertically and lower nurturing-processing storage unit has a larger volume than upper nurturing-processing storage unit. One of the groups (3) or (4) is moved up and down at predetermined time intervals. Larvae (B) are forced to displace from one of nurturing-processing storage units to next nurturing-processing storage unit which has been supplied with fresh food.

In FIG. 5 (*a*), the right side group (3) comprises, from the top, first nurturing-processing storage unit (31), third nurturing-processing storage unit (32), fifth nurturing-processing storage unit (33) and seventh nurturing-processing storage unit (34) stacked vertically. All nurturing-processing storage units (31), (32), (33) and (34) can be moved up and down simultaneously all together. As is shown in FIG. 5 (*b*), a fan (35) is arranged at an obliquely upper position to blow dried hot air. A feed recovering unit (36) is arranged below the seventh nurturing-processing storage unit (34).

The left side group (4) comprises, from the top, second nurturing-processing storage unit (41), fourth nurturing-processing storage unit (42), sixth nurturing-processing storage unit (43) and eighth nurturing-processing storage unit (44) stacked vertically. As is shown in FIG. 5 (*c*), a fan (45) is arranged at an obliquely upper position to blow dried hot air.

In case of the type shown in Example 2, larvae are displaced to next nurturing-processing storage unit at every 12 hours and a cycle from eggs (A) to a feed (7) is completed by 4 days. How to operate this system is explained with reference of FIGS. 5 (*a*) to (*e*).

In a condition shown in FIG. 5 (*a*), all of first nurturing-processing storage unit (31), of third nurturing-processing storage unit (32), of fifth nurturing-processing storage unit (33) and of seventh nurturing-processing storage unit (34) in the right side group (3) have been supplied with excreta (5) which are food. Imagoes (D) of housefly lay eggs at a fixed place in the egg-making unit (11) shown in FIG. 3. A predetermined amount of the resulting eggs (A) is introduced into the top first nurturing-processing storage unit (31).

Here, larvae (B) are nurtured and excreta (5) are consumed or ate by larvae (B) (the color of excreta (5) turns gradually white in FIGS). After excreta (5) are changed or consumed into organic fertilizer (6), the fan (35) is actuated to blow heated air, so that larvae (B) are forcibly dislodged from the first nurturing-processing storage unit (31) to an opposite second nurturing-processing storage unit (41), during which a partition is removed previously. At the same time, larvae (B) in the third nurturing-processing storage unit (32) are forcibly dislodged to an opposite fourth nurturing-processing storage unit (42), larvae (B) in the fifth nurturing-processing storage unit (33) are forcibly dislodged to an opposite sixth nurturing-processing storage unit (43), and larvae (B) in the seventh nurturing-processing storage unit (34) are forcibly dislodged to an opposite eighth nurturing-processing storage unit (44) respectively. The nurturing-processing storage units in the left side groups (4) have been supplied previously with fresh food. Excreta (5) in the left side group are consumed by larvae (B) to produce organic fertilizer which is recovered by a suitable recovering mean.

In next step shown in FIG. 5(*b*), all of the nurturing-processing storage units in the right side group (3) are elevated all together at one level. Emptied nurturing-processing storage units are supplied with fresh food or excreta (5). In the nurturing-processing storage units of left side group (4), larvae (B) are nurtured or fattened.

In next step shown in FIG. 5(*c*), after excreta (5) are changed to organic fertilizer (6), the fan (45) is actuated to blow heated air, so that larvae (B) are forcibly dislodged from the second nurturing-processing storage unit (41) to an opposite third nurturing-processing storage unit (32), during which a partition is removed previously. At the same time, larvae (B) in the fourth nurturing-processing storage unit (42) are forcibly dislodged to an opposite fifth nurturing-processing storage unit (33), and larvae (B) in the sixth nurturing-processing storage unit (43) are forcibly dislodged to an opposite seventh nurturing-processing storage unit (34).

Larvae (B) in the eighth nurturing-processing storage unit (44) are forcibly dislodged to a feed recovering unit (36).

Figure 5D:
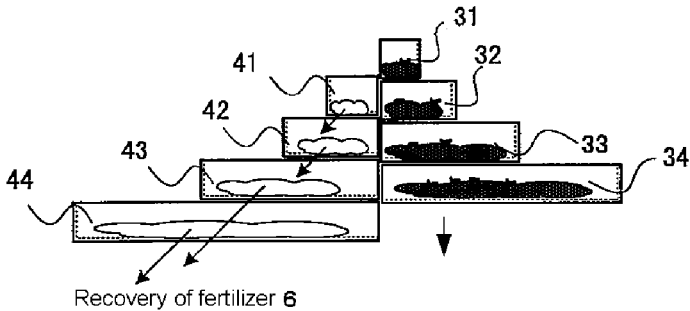
Figure 6:
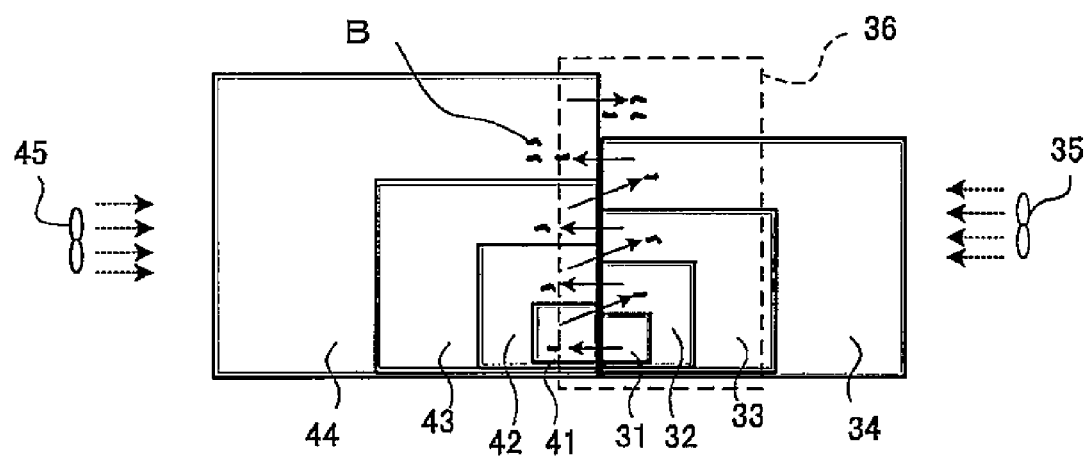
FIG. 6 is a plain view of FIG. 5A and FIG. 5B.

In next step shown in FIG. 5(d), organic fertilizer which is produced by consumption of excreta (5) by larvae (B) is recovered by a suitable recovering mean. Larvae (B) moved to the right side group are nurtured or fattened in the nurturing-processing storage units of right side group (3) and all of the nurturing-processing storage units in the right side group (3) are descended all together at one level.

Figure 5E:
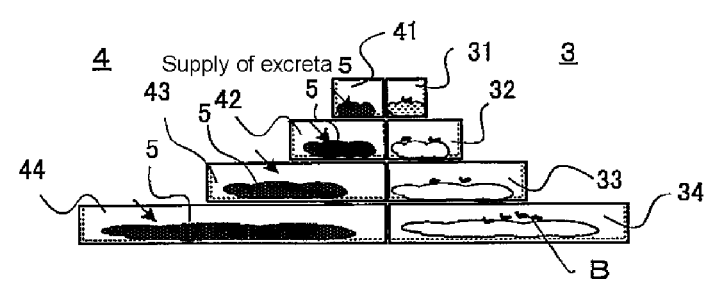

In next step shown in FIG. 5(e), emptied nurturing-processing storage units of the group (4) are supplied with fresh food or excreta (5). In the nurturing-processing storage units of right side group (3), larvae (B) are nurtured or fattened.

Now, it returned to the step of FIG. 5(a) and one cycle for producing organic fertilizer and a feed completes and then the above steps are repeated.

As explained above, the system for producing organic fertilizer and a feed shown in Example 2 has basically same functions and advantages as Example 1. However, in Example 2, all of opposite nurturing-processing storage units in the right side group (3) and in the left side group (4) respectively are actuated integrally simultaneously, so that their movement can be mechanized or atomized.

Note that the present invention is not limited to above Examples as a matter of course, but can be modified freely unless impair the characteristics of the present invention.

REFERENCE NUMBER

A eggs,
B larvae,
C pupae,
D imagoes,
11 egg producing unit,
2 nurturing-processing storage units,
21 first nurturing-processing storage unit,
22 second nurturing-processing storage unit,
23 third nurturing-processing storage unit,
24, 25 heater
26 feed collection section
3 nurturing-processing storage units,
31 first rearing nurturing-processing storage unit,
32 third nurturing-processing storage unit,
33 fifth nurturing-processing storage unit,
34 seventh nurturing-processing storage unit,
35 hot air fans,
36 feed recovery section,
4 nurturing-processing storage units,
41 second rearing nurturing-processing storage unit,
42 fourth nurturing-processing storage unit,
43 sixth nurturing-processing storage unit,
44 seventh nurturing-processing storage unit,
45 hot air fans,
5 excreta (food),
6 organic fertilizer,
7 feed

The invention claimed is:

1. A system for producing organic fertilizer from excreta of domestic animal by using insect larvae belonging to Diptera such as *Musca domestica* (housefly), Boettcherisca peregrine and *Tabanus*, and for producing grown larvae which can be used as a feed for cultured fish and chicken raising, comprising: a plurality of nurturing-processing storage units for nurturing larvae hatched from eggs, a means for dislodging only larvae forcibly from a former nurturing-processing storage unit to a later nurturing-processing storage unit successively with the progress of growth of larvae, wherein larvae leave said former nurturing-processing storage unit autonomously, and a transfer means for forcibly dislodging only larvae is selected from means to irradiate light, means to reduce the oxygen concentration, means to increase the concentration of ammonia, means to heat or cool, means to dry and means to decrease the quantity of food, these means being applied to the nurturing-processing storage unit into which forcibly larvae are forcibly dislodged.

2. The system for producing organic fertilizer and feed according to claim 1, wherein said means to irradiate light is chosen from natural light, blue light, ultraviolet ray and other light of limited wavelength.

3. The system for producing organic fertilizer and feed according to claim 1, wherein said means to heat or cool is chosen from heater, irradiation, heated stone, ice, cooled water, radiation air conditioning.

4. The system for producing organic fertilizer and feed according to claim 1, wherein said means to dry is to blowing of dry air.

5. The system for producing organic fertilizer and feed according to claim 1, wherein said food is chosen from organic wastes such as animal excreta, viscera of domestic animal, offal of fish, food residue, organic wastes such as sewage treatment residue.

6. A system for producing organic fertilizer from excreta of domestic animal as a food by using insect larvae belonging to Diptera such as *Musca domestica* (housefly), Boettcherisca peregrine and *Tabanus*, and for producing grown larvae which can be used as a feed for cultured fish and chicken raising, comprising:
a first nurturing-processing storage unit for raising larvae hatched from eggs, said first nurturing-processing storage unit being supplied at a predetermined time interval with a predetermined quantity of the food and a predetermined number of eggs,
a second nurturing-processing storage unit having a larger volume than said first nurturing-processing storage unit, larvae hatched from said eggs as well as said food being displaced or transferred from said first nurturing-processing storage unit to said second nurturing-processing storage unit, at a time when said larvae hatched from said eggs reach predetermined weights, wherein said second nurturing-processing storage unit is supplied with a fresh food to fatten up said larvae,
a third nurturing-processing storage unit into which only larvae are forcibly dislodged from said second nurturing-processing storage unit at a time when the food is consumed, wherein said third nurturing-processing storage unit is supplied with a fresh food to fatten further up said larvae,
wherein a digested residue of said food in said second nurturing-processing storage unit is recovered as a fertilizer, and said larvae are forcibly displaced from said third nurturing-processing storage unit into a recovery section at a time when the food is consumed, a digested residue of said food in said third nurturing-processing storage unit is recovered as a fertilizer, and said larvae in said recovery section are collected as a feed for other animal.

7. The system for producing organic fertilizer and feed according to claim 6, further comprising a transfer means for forcibly dislodging only larvae is selected from means to irradiate light, means to reduce the oxygen concentration, means to increase the concentration of ammonia, means to heat or cool, means to dry and means to decrease the quantity of food, these means being applied to the nurturing-processing storage unit into which forcibly larvae are forcibly dislodged.

8. The system for producing organic fertilizer and feed according to claim 7, wherein said means to irradiate light is chosen from natural light, blue light, ultraviolet ray and other light of limited wavelength.

9. The system for producing organic fertilizer and feed according to claim 7, wherein said means to heat or cool is chosen from heater, irradiation, heated stone, ice, cooled water, radiation air conditioning.

10. The system for producing organic fertilizer and feed according to claim 7, wherein said means to dry is to blowing of dry air.

11. The system for producing organic fertilizer and feed according to claim 6, wherein said food is chosen from organic wastes such as animal excreta, viscera of domestic animal, offal of fish, food residue, organic wastes such as sewage treatment residue.

12. A system for producing organic fertilizer from excreta of domestic animal as a food by using insect larvae belonging to Diptera such as *Musca domestica* (housefly), Boettcherisca peregrine and *Tabanus*, and for producing grown larvae which can be used as a feed for cultured fish and chicken raising, comprising:
   a first nurturing-processing storage unit for raising larvae hatched from eggs, said first nurturing-processing storage unit being supplied at a predetermined time interval with a predetermined quantity of the food and a predetermined number of eggs,
   a second nurturing-processing storage unit having a larger volume than said first nurturing-processing storage unit and being supplied with a fresh food to fatten up said larvae,
   wherein only larvae hatched from said eggs are displaced from said first nurturing-processing storage unit to said second nurturing-processing storage unit at a time when said larvae hatched from said eggs reach predetermined weights, and a digested residue of said food in said second nurturing-processing storage unit is recovered as a fertilizer,
   a third nurturing-processing storage unit into which only larvae are forcibly dislodged from said second nurturing-processing storage unit at a time when the food is consumed,
   wherein said third nurturing-processing storage unit is supplied with a fresh food to fatten further up said larvae, a digested residue of said food in said third nurturing-processing storage unit being recovered as a fertilizer,
   the above processing being repeated in further nurturing-processing storage unit having a larger volume than former nurturing-processing storage unit until the final nurturing-processing storage unit which is supplied with a largest amount of a fresh food to fatten up said larvae,
   wherein only larvae are forcibly dislodged from said final nurturing-processing storage unit to a recovery section at a time when the food is consumed, a digested residue of said food in said final nurturing-processing storage unit being recovered as a fertilizer, while said larvae in said recovery section are collected as a feed for other animal.

13. The system for producing organic fertilizer and feed according to claim 12, in which a nurturing-processing storage unit into which larvae are forcibly dislodged is positioned at an opposite location, and, after a transfer of larvae completed, a next nurturing-processing storage unit is positioned at an opposite location.

14. The system for producing organic fertilizer and feed according to claim 12, further comprising a transfer means for forcibly dislodging only larvae is selected from means to irradiate light, means to reduce the oxygen concentration, means to increase the concentration of ammonia, means to heat or cool, means to dry and means to decrease the quantity of food, these means being applied to the nurturing-processing storage unit into which forcibly larvae are forcibly dislodged.

15. The system for producing organic fertilizer and feed according to claim 14, wherein said means to irradiate light is chosen from natural light, blue light, ultraviolet ray and other light of limited wavelength.

16. The system for producing organic fertilizer and feed according to claim 14, wherein said means to heat or cool is chosen from heater, irradiation, heated stone, ice, cooled water, radiation air conditioning.

17. The system for producing organic fertilizer and feed according to claim 14, wherein said means to dry is to blowing of dry air.

18. The system for producing organic fertilizer and feed according to claim 12, wherein said food is chosen from organic wastes such as animal excreta, viscera of domestic animal, offal of fish, food residue, organic wastes such as sewage treatment residue.

* * * * *